(12) United States Patent
Bock et al.

(10) Patent No.: US 7,709,679 B2
(45) Date of Patent: May 4, 2010

(54) PROCESS FOR SIMULTANEOUSLY PREPARING 4,4'-DIPHENYLMETHANEDIAMINE AND DIPHENYLMETHANE DIISOCYANATE AND POLYPHENYLENEPOLYMETHYLENE POLYISOCYANATES

(75) Inventors: Michael Bock, Ruppertsberg (DE); Hans-Juergen Pallasch, Kallstadt (DE); Filip Deberdt, Muizen (BE); Johnny Moors, Antwerp (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/160,163

(22) PCT Filed: Jan. 12, 2007

(86) PCT No.: PCT/EP2007/050277

§ 371 (c)(1),
(2), (4) Date: Jul. 7, 2008

(87) PCT Pub. No.: WO2007/085534

PCT Pub. Date: Aug. 2, 2007

(65) Prior Publication Data

US 2009/0005596 A1 Jan. 1, 2009

(30) Foreign Application Priority Data

Jan. 20, 2006 (EP) .................................. 06100663

(51) Int. Cl.
*C07C 263/10* (2006.01)
*C07C 209/60* (2006.01)
(52) U.S. Cl. ................. 560/347; 564/396; 564/397
(58) Field of Classification Search ........................ None
See application file for complete search history.

(56) References Cited

U.S. PATENT DOCUMENTS 4,014,914 A * 3/1977 Pistor et al. ................. 560/347
4,034,039 A 7/1977 Sun
4,201,722 A * 5/1980 Sun ............................ 564/334

FOREIGN PATENT DOCUMENTS

| BE | 855 402 | | 12/1977 |
|---|---|---|---|
| DE | 19 01 993 | | 8/1970 |
| DE | 100 31 540 | | 1/2002 |
| EP | 0 572 030 | | 12/1993 |
| GB | 1 169 127 | | 10/1969 |
| GB | 1287192 | * | 8/1972 |
| RO | 104327 | | 12/1993 |
| SU | 463 658 | | 9/1975 |

* cited by examiner

*Primary Examiner*—Brian J Davis
(74) *Attorney, Agent, or Firm*—Oblon, Spivak, McClelland, Maier & Neustadt, L.L.P.

(57) ABSTRACT

The invention provides a process for the simultaneous preparation of 4,4'-diphenylmethanediamine and also diphenylmethane diisocyanate and polyphenylenepolymethylene polyisocyanates, which comprises the steps
a) preparation of a mixture of diphenylmethanediamine and polyphenylenepolymethylenepolyamines by acid condensation of aniline and formaldehyde and subsequent work-up of the mixture,
b) splitting-off of part of the mixture prepared in step a),
c) distillation of the mixture separated off in step b) in a column,
d) recirculation of the bottom product from step c) to the end product from step a) and condensation of the overhead product from step c),
e) distillation of the overhead product from step c) in a column,
f) recirculation of the overhead product from step e) to the end product from step a),
g) isolation of the 4,4'-diphenylmethanediamine obtained as bottom product in step e),
h) reaction of the mixture from step a) with phosgene and subsequent work-up of the reaction product.

15 Claims, No Drawings

PROCESS FOR SIMULTANEOUSLY PREPARING 4,4'-DIPHENYLMETHANEDIAMINE AND DIPHENYLMETHANE DIISOCYANATE AND POLYPHENYLENEPOLYMETHYLENE POLYISOCYANATES

DESCRIPTION

The invention relates to a process for the simultaneous preparation of 4,4'-diphenylmethanediamine and also diphenylmethane diisocyanate and polyphenylenepolymethylene polyisocyanates.

Diphenylmethane diisocyanate and polyphenylenepolymethylene polyisocyanates, hereinafter also referred to as MDI, are produced in large quantities and are used, in particular, for the production of polyurethanes. The industrial preparation of these compounds is carried out, in particular, by reacting the corresponding amines with phosgene. The products are always mixtures of 2-ring and multiring compounds. The mixtures of 2-ring und multiring MDA will hereinafter also be referred to as crude MDA.

The mixtures of isomers of diphenylmethanediamine and its higher homologues, hereinafter also referred to as MDA, which are used for preparing MDI are usually prepared by acid-catalyzed reaction of aniline with formaldehyde and subsequent neutralization and work-up of the reaction product. This work-up product is usually dissolved in a solvent and is converted in this form into MDI.

For particular applications, for example as crosslinkers in plastics or surface coatings, it is also possible to use 2-ring MDA.

A number of methods of separating off 2-ring MDA are known from the prior art.

Thus, the isolation of 2-ring MDA and purification of the 4,4'-MDA can be effected by means of extraction as described, for example, in SU 463 658, by means of reaction with metal salts as described in GB 1 169 127, by melting as described in EP 572 030 or by treatment with solvents as described in BE 855 402 and U.S. Pat. No. 4,034,039.

RO 104327 describes the isolation of 2-ring MDA by means of thin film distillation.

It is also known that 2-ring MDA can be separated off from the crude MDA by means of distillation.

DE 1 901 993 describes a process for preparing 4,4'-MDA, in which the 2-ring MDA is distilled off from a mixture of 2-ring MDA and multiring MDA and the 4,4'-MDA is separated off from the distillation product by crystallization. The distillation is carried out at 2 torr and 220-230° C.

DE 100 31 540 describes a process for separating off 2,2'-MDA and 2,4'-MDA from crude MDA. A distillation column having at least 40 theoretical plates can be used for this purpose. The distillation is carried out at a temperature of 180-280° C., a pressure at the top of 0.1-10 mbar and a pressure at the bottom of 8-20 mbar. To reduce the pressure drop, low-pressure-drop mesh packings are used. The crude MDA which has been freed of 2,2'- and 2,4'-MDA is reacted with phosgene to give MDI, and the 2,2'- and 2,4'-MDA which have been separated off are recirculated to the condensation stage.

A disadvantage of all previous processes for separating off 2-ring MDA and for separating the isomers is that a separate process which is complicated in terms of apparatus and in which the by-products obtained usually have to be disposed of has been necessary for this purpose.

It was an object of the present invention to provide a process for preparing 2-ring MDA having a high proportion, in particular at least 80%, of 4,4'-MDA, which process requires a small chemical engineering outlay. In addition, it should be possible to produce 2-ring MDA with different mixtures in a simple way.

The object has been able to be achieved by a simultaneous process for preparing MDI and 2-ring MDA.

The invention accordingly provides a process for the simultaneous preparation of 4,4'-diphenylmethanediamine and also diphenylmethane diisocyanate and polyphenylenepolymethylene polyisocyanates, which comprises the steps a) preparation of a mixture of diphenylmethanediamine and polyphenylenepolymethylenepolyamines by acid condensation of aniline and formaldehyde and sub-sequent work-up of the mixture,
b) splitting-off of part of the mixture prepared in step a),
c) distillation of the mixture separated off in step b) in a column,
d) recirculation of the bottom product from step c) to the end product from step a) and condensation of the overhead product from step c),
e) distillation of the overhead product from step c) in a column,
f) recirculation of the overhead product from step e) to the end product from step a),
g) isolation of the 4,4'-diphenylmethanediamine obtained as bottom product in step e),
h) reaction of the mixture from step a) with phosgene and subsequent work-up of the reaction product.

The process can be configured in various ways. In one embodiment of the process, all steps of the process can be operated continuously.

If 2-ring MDA is not to be produced all the time, it is possible to shut down the process steps b) to g) for part of the time and to react all the product produced in process step a) with phosgene during this time.

The distillation in the process steps c) and e) can preferably be carried out in two different columns. To vaporize the vapors, it is possible to use evaporators which have a short residence time and do not subject the product to harsh conditions, in particular falling film evaporators. It is in principle also possible to carry out both steps in a dividing wall column.

A particularly mild distillation of the 4,4'-MDA can be achieved at pressures at the bottom of <8 mbar, in particular <6 mbar. This is preferably achieved by use of particularly low-pressure-drop, structured packing elements and liquid distributors. The pressure drop over all packing elements, collectors, distributors and the condenser is preferably 0.5-3 mbar, particularly preferably less than 0.8 mbar, in the separation column of step c). In the separation column of step e), the pressure drop over all packing elements, collectors, distributors and the condenser is preferably less than 5 mbar, particularly preferably less than 3.5 mbar. The pressure at the top of the columns in steps c) and e) is preferably 3 mbar abs.

The number of theoretical plates required in the separation column of step c) is preferably from 1 to 5, particularly preferably 2-3, and in the separation column of step e) is preferably 9-20, particularly preferably 10-13.

The temperatures at the bottom in the two columns are preferably 200-250° C., more preferably 220-240° C. In the column of step c), the temperature at the bottom is particularly preferably from 235 to 240° C. The temperature at the top of the column of step c) is preferably from 200 to 210° C. and that at the top of the column of step e) is preferably from 190 to 210° C.

Under the stated conditions, 4,4'-MDA having a purity of at least 79% by weight can be obtained at the end of step c) and 4,4'-MDA having a purity of at least 98% can be obtained at the end of step e). If a 2-ring MDA having a different isomer distribution is to be provided, this can preferably be achieved by mixing the product streams. Here, preference is given to mixing the bottom product of step e) with the overhead product from step e) or particularly preferably with the overhead product from step c).

The purity of the 4,4'-MDA obtained in step e) is completely independent of the content of 2-ring MDA in the reaction product from step a). Even in the case of small proportions, for example from 50 to 60% by weight, or in the case of greatly fluctuating proportions of 2-ring MDA in the product from step a), the remaining process steps are not adversely affected.

In step a) in the process of the invention, aniline is reacted with formaldehyde in a customary way using acid catalysts to give MDA. This process is generally known and is described, for example, in DE 100 31 540. Variation of the ratio of acid to aniline and of formaldehyde to aniline enables the proportion of the 2-ring product in the crude MDA to be adjusted as desired.

The amount of the substream taken off in step b) is dependent on the amount of 4,4'-MDA required. To avoid an excessively large change in the composition of the MDI formed in step h), the amount taken off should be no greater than 20% by weight, preferably <15% by weight. An influence on the composition of the product from step h) can also be countered by selecting the reaction conditions in step a) so that a high proportion of 4,4'-MDA is formed. This can be achieved by increasing the ratio of acid to aniline. A higher ratio means that more 4,4'-MDA than 2,4'-MDA is formed. The total 2-ring MDA content then increases slightly. A larger total amount of 2-ring MDA can be formed by increasing the ratio of aniline to formaldehyde. The proportion of 2-ring MDA in the product from step a) is preferably from 50 to 60% by weight.

A preferred embodiment of the process of the invention will be described below.

A substream of from greater than 0 to 20% by weight, depending on the load range in which the plant is running, is split off from an MDA mixture from the acid-catalyzed condensation of aniline and formaldehyde. This usually has a temperature in the range from 120 to 200° C. It is heated to 150-220° C. in a heat exchanger.

The feedstream is fed to a column having a structured packing in order to separate off the 2-ring MDI, and is mixed beforehand with the bottom product from this column. The mixture obtained in this way is heated to 235-240° C. in the bottom of the column by means of a falling film evaporator.

As packing, it is possible to utilize commercial structured packings, for example from Sulzer or Montz.

The more readily volatile components, essentially 2-ring MDA, go over at the top of the column, while the less volatile components, essentially multiring MDA with a proportion of 2-ring MDA, remain in the bottom of the column and are discharged as a PMDA mixture. Part of the bottom product is discharged and added to the PMDA stream to the phosgenation. The remainder of the bottom product is, as described, mixed with the feedstream and fed back into the column. A pressure of about 3 mbar abs. prevails at the top of the column.

The bottom product discharged passes part of the heat to the feedstream via a heat exchanger.

The overhead product is virtually completely condensed in an integrated heat exchanger. In a downstream heat exchanger, remaining traces of MMDA and aniline are condensed out from the gas phase. The condensation takes place at from 90 to 100° C. An offgas stream which comprises about 97% of leakage air and about 3% of organic components is obtained.

The overhead product condensed in the first heat exchanger is divided into two sub streams.

The first stream forms the feed to a further column in which the 2-ring MDA is distilled (step e). A pressure of about 3 mbar abs. prevails at the top of this column. The column is likewise packed with a structured packing. A falling film evaporator which is supplied with steam is used for heating the feed to the column. The column has a bottom temperature of about 220° C. The lower-boiling mixture of 2,2'-, 2,4'- and sometimes also 4,4'-MDA is virtually completely condensed as overhead product in a heat exchanger located downstream of column 2.

The condensed overhead product is likewise added to the PMDA stream to the phosgenation.

The bottom product from the column of step e) comprises about 98% of 4,4'-MDA and can be sold directly.

To set isomer ratios other than 98% of 4,4'-MDA to the remaining 2-ring MDA, the bottom product from the second column can be mixed with a substream of the overhead product from the first column.

EXAMPLE 1

Preparation of Pure 4,4'-diphenylmethanediamine Having a High Content of the 4,4'-isomer (98.0%)

From the PMDA stream to the phosgenation of 20 t/h (a), 1750 kg/h (8.75% by weight) are continuously branched off to the diphenylmethanediamine distillation (b). This comprises 10% by weight of 2,4'-diphenylmethanediamine, 47.3% by weight of 4,4'-diphenylmethanediamine and 0.6% by weight of 2,2'-diphenylmethanediamine and also residual amounts of 3-ring and multiring compounds of polyphenylmethanediamine.

The mixture is preheated to 150° C. and then pumped into the pumped circuit of a falling film evaporator of the column c). The inlet temperature into the column c) is 220° C.

At the top of the column c), a mixture of 785 kg/h of 2-ring isomers comprising 80% by weight of 4,4'-diphenylmethanediamine is taken off. A small amount of incondensable components also goes into the offgas.

960 kg/h of 3-ring and multiring components and also small amounts of 2-ring diphenylmethanediamine (about 24% by weight) are accordingly obtained at the bottom of the column and this stream goes to the phosgenation (d).

Column c) is operated at a pressure at the top of 4 mbar and a temperature at the bottom of 240° C.

The overhead condensate from c) is rectified in the column e). This column is operated at a pressure at the top of 4 mbar and a temperature at the bottom of 230° C. 455 kg/h of a mixture comprising 98.0% by weight of 4,4'-diphenylmethanediamine are obtained at the bottom (g). At the top of the column, the unsharp fraction comprising 2-ring diphenylmethanediamine with 53% by weight of 4,4'-diphenylmethanediamine, in a total amount of 330 kg/h, is recirculated to a).

EXAMPLE 2

Simultaneous Preparation of Two 4,4'-diphenylmethanediamine Grades: 4,4'-Diphenylmethanediamine of 98.0% by Weight Purity and 4,4'-diphenylmethanediamine of 90% by Weight Purity From the PMDA stream to the phosgenation (a) of 20 t/h, 1750 kg/h (8.75% by weight) are continuously branched off to the diphenylmethanediamine distillation. This comprises 10% by weight of 2,4'-diphenylmethanediamine, 47.3% by weight of 4,4'-diphenylmethanediamine and 0.6% by weight of 2,2'-diphenylmethanediamine and also residual amounts of 3-ring and multiring compounds.

The mixture is preheated to 150° C. and then pumped into the pumped circuit of the falling film evaporator of the column c). The inlet temperature into the column c) is 220° C.

At the top of the column c), a mixture of 785 kg/h of 2-ring isomers comprising 80% by weight of 4,4'-diphenylmethanediamine is taken off. A small amount of incondensable components also goes into the offgas. 960 kg/h of 3-ring and multiring components and also small amounts of 2-ring diphenylmethanediamine (about 24% by weight) are accordingly obtained at the bottom of the column and this stream goes to the phosgenation (d). Column c) is operated at a pressure at the top of 4 mbar and a temperature at the bottom of 240° C.

Only part of the overhead condensate from c) is then rectified in the column e). Of the 785 kg/h, 695 kg/h are fed to the column. The column (e) is operated at a pressure at the top of 4 mbar and a temperature at the bottom of 230° C. 399 kg/h of a mixture comprising 98.0% of 4,4'-diphenylmethanediamine (product 1) are obtained at the bottom of the column.

30% by weight of the stream from the bottom of the column are now mixed with the product which has not been fed to the column (90 kg/h). This gives a further mixture comprising 90% of 4,4'-diphenylmethanediamine (product 2).

The result is that two product grades are obtained from one stream a), namely 279 kg/h of 98% by weight pure 4,4'-diphenylmethanediamine and 209 kg/h of 90.3% by weight pure 4,4'-diphenylmethanediamine.

The invention claimed is:

1. A process for the simultaneous preparation of 4,4'-diphenylmethanediamine, diphenylmethane diisocyanate and polyphenylenepolymethylene polyisocyanates, which comprises the steps
    a) preparation of a mixture of diphenylmethanediamine and polyphenylenepolymethylenepolyamines by acid condensation of aniline and formaldehyde,
    b) splitting-off of part of the mixture prepared in step a),
    c) distillation of the mixture split-off in step b) in a column,
    d) recirculation of the bottom product from step c) to the end product from step a) and condensation of the overhead product from step c),
    e) distillation of the overhead product from step c) in a column,
    f) recirculation of the overhead product from step e) to the end product from step a),
    g) isolation of the 4,4'-diphenylmethanediamine obtained as bottom product in step e),
    h) reaction of the remaining mixture from step a) with phosgene and subsequent isolation of diphenylmethane diisocyanate and polyphenylenepolymethylene polyisocyanates.

2. The process according to claim 1, wherein all steps of the process are carried out continuously.

3. The process according to claim 1, wherein the mixture of diphenylmethanediamine and polyphenylenepolymethylenepolyamines enters the column in step c) at a temperature in the range from 160 to 180° C.

4. The process according to claim 1, wherein a pressure of 1-5 mbar abs. prevails at the top of the column in step c).

5. The process according to claim 1, wherein a temperature of from 200 to 210° C. prevails at the top of the column in step c).

6. The process according to claim 1, wherein the pressure drop over all packing elements, collectors, distributors and the condenser of the column in step c) is less than 0.9 mbar.

7. The process according to claim 1, wherein the column in step c) has a temperature at the bottom of from 235 to 240° C.

8. The process according to claim 1, wherein the column in step c) has a separation power of 2-3 theoretical plates.

9. The process according to claim 1, wherein the columns in steps c) and e) have a low-pressure-drop structured packing.

10. The process according to claim 1, wherein a pressure of 1-4 mbar abs. prevails at the top of the column in step e).

11. The process according to claim 1, wherein a temperature of 190-210° C. prevails at the top of the column in step e).

12. The process according to claim 1, wherein the pressure drop over all packing elements, collectors, distributors and the condenser of the column in step e) is less than 3.5 mbar.

13. The process according to claim 1, wherein the column in step e) has a temperature at the bottom of 220-240° C.

14. The process according to claim 1, wherein the column in step e) has a separation power of 10-13 theoretical plates.

15. The process according to claim 1, wherein part of the overhead product from the column in step e) is mixed with all or part of the bottom product from the column in step c).

* * * * *